United States Patent [19]

Grunenberg et al.

[11] Patent Number: 5,599,824
[45] Date of Patent: Feb. 4, 1997

[54] PHARMACEUTICAL PREPARATION CONTAINING A SPECIFIC CRYSTAL MODIFICATION OF ISOPROPYL-(2-METHOXYETHYL) 1,4-DIHYDRO-2, 6-DIMETHYL-4-(3-NITROPHENYL)-3,5-PYRIDINEDICARBOXYLATE

[75] Inventors: Alfons Grunenberg, Dormagen; Ahmed Hegasy, Leverkusen; Wolfgang Mück; Gerhard Franckowiak, both of Wuppertal; Rango-Rao Kanikanti, Leverkusen, all of Germany

[73] Assignee: Bayer Aktiengesellschaft, Leverkusen, Germany

[21] Appl. No.: 380,229

[22] Filed: Jan. 30, 1995

Related U.S. Application Data

[63] Continuation of Ser. No. 939,234, Sep. 2, 1992, abandoned.

[30] Foreign Application Priority Data

Sep. 11, 1991 [DE] Germany .......................... 41 30 173.0

[51] Int. Cl.⁶ .................................................. A61K 31/44
[52] U.S. Cl. ........................... 514/356; 514/951; 546/321
[58] Field of Search ................... 514/356, 951; 546/321

[56] References Cited

U.S. PATENT DOCUMENTS

| 3,932,645 | 1/1976 | Meyer et al. | 424/266 |
| 4,406,906 | 9/1983 | Meyer et al. | 424/263 |

FOREIGN PATENT DOCUMENTS

| 0004650 | 10/1979 | European Pat. Off. . |
| 0047899 | 3/1982 | European Pat. Off. . |
| 0167909 | 1/1986 | European Pat. Off. . |
| 2139892 | 11/1984 | United Kingdom . |
| 2211188 | 6/1989 | United Kingdom . |

OTHER PUBLICATIONS

Journal of Computed–Aided Molecular Design, vol. 4, No. 3, 1990; pp. 215–230; D. A. Langs et al. 'Receptor Model for the Molecular Basis of Tissue Selectivity of 1, 4–Dihydropyridine Calcium Channel Drugs'.

Wang, et al., Acta Cryst, vol. C45, 1989, pp. 1748–1751 'Structure of the Calcium Channel Antagonist, Nimodipine'.

The Merck Index (1989), Merck & Co., Inc., Rahway, N.J., USA, p. 1036.

W. Bahr et al., Organische Stereochemie, 1973, Springer Publishers, pp. 93 and 94 (English translation).

Wang et al., "Structure of Calcium Antagonist, Nimodipine", Acta Crystallographica, Nov. 1989, vol. C45, Part 11, pp. 1748–1751.

*Primary Examiner*—Marianne M. Cintins
*Assistant Examiner*—M. Moezie
*Attorney, Agent, or Firm*—Sprung Horn Kramer & Woods

[57] ABSTRACT

The invention relates to pharmaceutical preparations, containing a specific crystal modification (subsequently called "modification II") of isopropyl-(2-methoxyethyl) 1,4-dihydro-2,6-dimethyl-4-(3-nitrophenyl)-3,5-pyridinedicarboxylate (nimodipine) and to a process for its preparation.

2 Claims, 1 Drawing Sheet

PHARMACEUTICAL PREPARATION CONTAINING A SPECIFIC CRYSTAL MODIFICATION OF ISOPROPYL-(2-METHOXYETHYL) 1,4-DIHYDRO-2, 6-DIMETHYL-4-(3-NITROPHENYL)-3,5-PYRIDINEDICARBOXYLATE

This application is a continuation, of application Ser. No. 07/939,234, filed on Sep. 2, 1992 now abandoned.

The invention relates to pharmaceutical preparations, containing a specific crystal modification (subsequently called "modification II") of isopropyl-(2-methoxyethyl) 1,4-dihydro-2,6-dimethyl-4-(3-nitrophenyl)-3,5-pyridinedicarboxylate (nimodipine) and to a process for its preparation.

Nimodipine, its preparation and its use as a cerebral therapeutic have already been disclosed (cf. EP-B-4650 and GB 1,358,951). The nimodipine crystals employed hitherto in pharmaceutical preparations (modification I) have a melting point of 125° C. (cf. the Merck Index (1989) 1036). Wang et al. [S. D. Wang, L. G. Herbette, D. G. Rhodes, Acta Cryst. C 45, 1748 (1989)] described the X-ray structure of a nimodipine enantiomer (melting range 134°–136° C.) which is identical to the X-ray structure of modification II of the racemic form.

The crystal modification I having a melting point of 125° C., which was hitherto exclusively used for the preparation of pharmaceutical forms, is not satisfactory in the preparation of various pharmaceutical forms. Thus, for example, in the case of suspensions for oral administration which contain nimodipine in modification I, crystal growth and as a result increased sedimentation are observed under storage conditions, which leads to solid deposits at the bottom of the storage vessel, as a result of which the quality and dosage accuracy and also the biological activity of these preparations are considerably impaired.

The physical instability of the nimodipine modification I known hitherto in aqueous suspensions, which occurs preferably if the preparations are exposed to a temperature loading or stored over a relatively long period, impairs the absorption, activity and safety of these preparations. It is therefore of great importance to use a suspension which is as stable as possible for the preparation of pharmaceutical forms containing nimodipine.

The nimodipine modification II is nearly white and surprisingly less light-sensitive and chemically and physically more stable compared with the known yellow modification I. It has a melting point of about 116° C. It is very highly suitable for the preparation of stable and storable pharmaceutical preparations which contain nimodipine crystals, in particular for suspensions.

The invention accordingly relates to stable pharmaceutical preparations which contain the crystalline modification II of isopropyl-(2-methoxyethyl) 1,4-dihydro-2,6-dimethyl-4-(3-nitrophenyl)-3,5-pyridinedicarboxylate (nimodipine) of melting point about 116° C. having an average particle size of at most 5 µm, in particular those preparations in which crystals having an average particle size of 0.1 to 5.0 µm, preferably 0.3 to 3.0 µm, are necessary, such as, for example, suspensions or solid pharmaceutical forms.

The crystals of the modification II to be used according to the invention are prepared, for example, by suspending nimodipine of the customary modification I in inert organic solvents, for example in acetone or lower alcohols preferably having 1 to 6C atoms, if appropriate in the presence of water and by treating at temperatures of 0° to 80° C., preferably 10° to 60° C., in particular 20° to 50° C., until quantitative conversion to modification II occurs, and if appropriate separating off the crystals of modification II obtained according to customary methods and drying to constant weight at temperatures between 20° and 70° C. to remove the solvent present.

The conversion time is as a rule about 2 to 24 hours and is dependent on the nature of the solvent and the temperature selected.

To prepare pharmaceutical forms, nimodipine modification II is suspended in a suitable suspending liquid, if appropriate with the addition of pharmaceutical auxiliaries, and the suspension is ground to the desired maximum average particle size according to the invention, for example by bead grinding (perlmilling).

The crystal modification II has a characteristic IR spectrum which differs distinctly from the spectrum of modification I.

The X-ray structural analyses also show that the molecular conformation and arrangement of the molecules in the crystal lattices of modifications I and II are different.

The melting point of modification II is 116° C. and can thus be clearly differentiated from 125° C. (in some publications, ranges of 123° to 127° C. are given) of modification I. The pure enantiomers of nimodipine melt at 134°–136° C.

The thermogram of modification II recorded by means of DSC (Differential Scanning Calorimetry) under atmospheric pressure shows, in agreement with the melting point determination, an endothermic melting peak at 116° C. and differs clearly from the thermogram of modification I.

The X-ray diffractogram and $^{13}$C solid NMR spectra are characteristically different for the nimodipine crystal modifications I and II.

To date, only nimodipine preparations are commercially available which contain the active substance in amorphous or dissolved form. Nimodipine is on the one hand offered for sale as drops or solution in capsules, i.e. dissolved in a mixture of specific organic solvents, and as a coprecipitate ("solid solution") in solid polyvinyl-pyrrolidone in tablet form. The preparation of the coprecipitate tablets is associated with great technical expenditure and the liquid nimodipine solutions show a very rapid rise in the plasma level, which often leads to undesired effects. The object of the invention is thus the making available of a preparation form for the extremely poorly soluble and problematic active substance nimodipine, which a) can be prepared in a simple manner, b) has a good bioavailability, c) guarantees a moderate rise in the plasma level, d) can be easily metered and administered and e) has a good storage stability.

In pharmaceutical preparations, for example during storage in comparison to modification I, the crystal modification II of nimodipine according to the invention shows a higher physical and chemical stability and is therefore safer in use and thus better suited for the preparation of various pharmaceutical forms, in particular suspensions.

The invention also relates to orally administrable liquid and solid pharmaceutical preparations which contain crystal modification II, such as, for example, suspensions, tablets, coated tablets, hard and soft gelatine capsules and the like. Use in suspensions is of particular utility.

When using several, different pharmaceutical preparations of an active substance, the bioequivalence of the pharmaceutical formulations, i.e. the biometrically safeguarded uniformity of systemically available dose and maximum plasma concentration, is of great importance for the therapeutic equivalence of the pharmaceutical preparations.

Using the suspension containing bead-ground nimodipine/crystal modification II mentioned in Exemplary Embodiment 1, a pharmaceutical formulation which can be employed orally is available which is equivalent to the nimodipine commercial tablet (cf. EP Patent No. 167 909-B) with respect to its pharmacokinetic properties; i.e. in addition to the simple preparation ability (a) and the good storage stability (e) it also fulfils the conditions b), c) and d).

TABLE*

|  | Crystal suspension (nimodipine/ modification II) | Commercial tablet |
| --- | --- | --- |
| relative bio-availability | 94.2/1.40 | 100 |
| maximum plasma concentration [μg/l] | 11.0/1.71 | 11.3/1.55 |

(*numerical data: geometric average value/geom. standard deviation)

Figure 1:
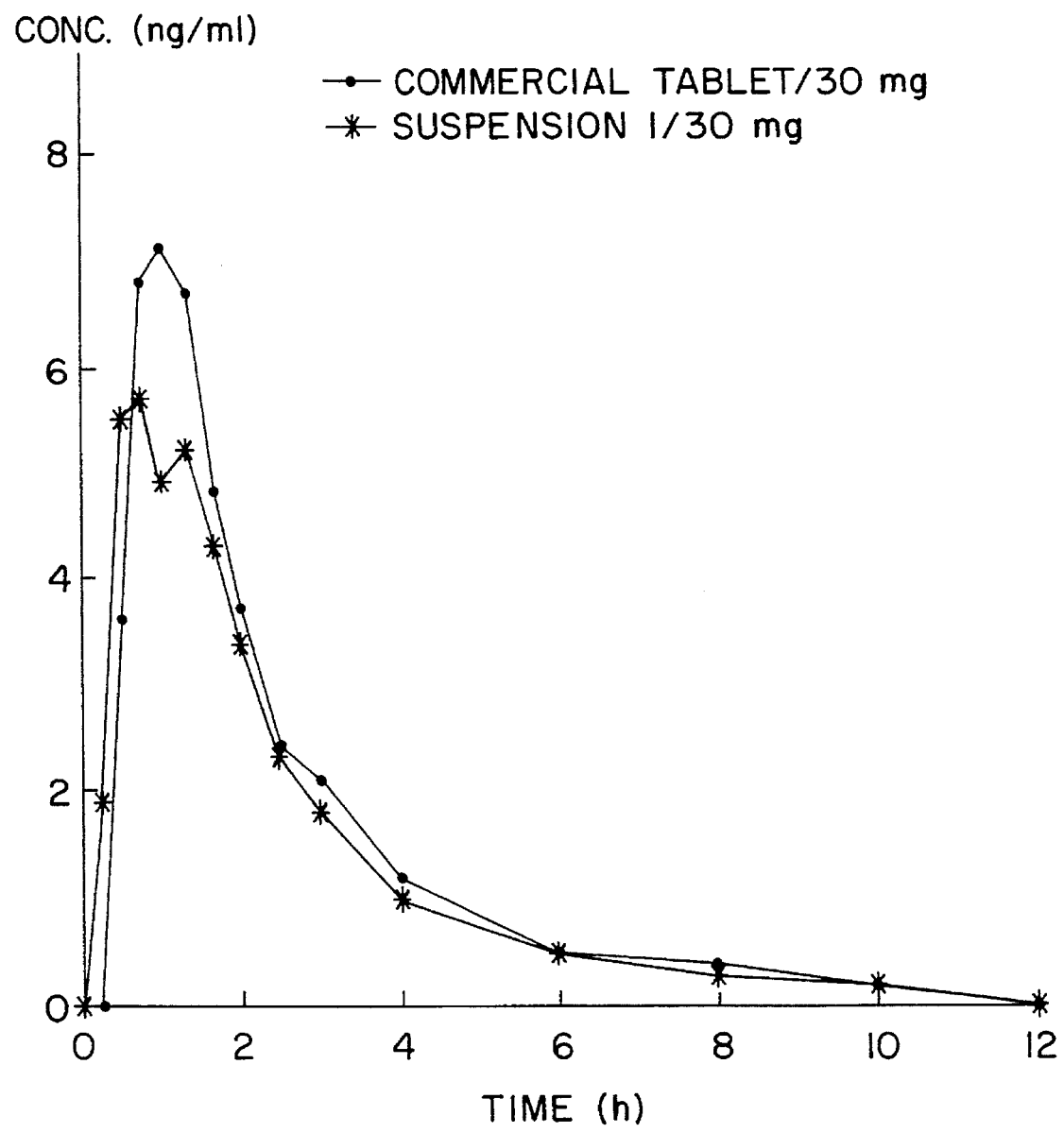
FIG. 1 shows the nimodipine plasma concentrations (geometric average values) of the commercial tablet/30 mg and the suspension according to the invention/30 mg.

In addition to nimodipine of modification II, the pharmaceutical preparations according to the invention optionally contain one or more other active substances as such or are optionally formulated together with auxiliaries and additives customarily employed in pharmacy, such as binders, fillers, preservatives, disintegrants, flow regulators, plasticisers, wetting agents, dispersants, emulsifiers, solvents, flavourings and the like to give customary administration forms for oral or parenteral administration.

The pharmaceutical preparations are prepared in a manner known per se, for example by mixing, stirring in, suspending, emulsifying etc. the active substances with or in the pharmaceutical auxiliaries and processing to give pharmaceutically suitable administration forms for oral, parenteral or rectal administration.

It was not foreseeable that for the known active substance nimodipine, which has been known for many years, a stable crystal modification which has hitherto not been employed in pharmaceutical preparations existed, which, together with identical biological action, has a lower light sensitivity and a better storage stability. In particular in the case of suspensions, undesired crystal growth and the formation of other crystal forms is avoided by the use of modification II. The safety of nimodipine preparations is increased by the use of modification II and the risk for the patients is thus decreased.

The following exemplary embodiments illustrate the subject-matter of the invention.

EXEMPLARY EMBODIMENTS

Example 1

3 g of hydroxypropylcellulose L fine and 0.5 g of Solbrol M are dissolved in about 450 ml of demineralised water, and 30 g of microfinely ground nimodipine of modification II are suspended in this solution. In addition, 12 g of hydroxypropylcellulose M fine, 1 g of citric acid, 0.5 g of Solbrol M and 2 g of trisodium citrate are dissolved in about 500 ml of demineralised water. The nimodipine-containing suspension is bead-ground and then mixed at room temperature with the suspending liquid. The average particle size is 0.9 μm.

Example 1a (negative example)

Analogously to example 1, 30 g of nimodipine of modification I are suspended and ground by means of a bead mill.

After dilution with the remaining suspending liquid, the suspensions are filled into bottles and stored at about 40° C. Already after 3 weeks, nimodipine consists of crystals of an average particle size of about 20 μm.

Example 2

The suspension, consisting of 2 g of Arlacel 20, 6 g of Tylopur C 300 P, 1 g of citric acid, 2 g of trisodium citrate, 0.5 g of Solbrol M and 30 g of microfinely ground nimodipine of modification II are subjected to bead grinding in about 500 ml of demineralised water and then mixed with stirring at room temperature with the suspending liquid, consisting of about 460 ml of demineralised water, 6 g of Tylopur C 300 P and 0.5 g Solbrol M. (Average particle size 1.7 μm).

Example 3: (Suspension drops containing 6% nimodipine)

14.4 g of Solbrol M are dissolved in 1593.6 g of hot water. 72 g of hydroxypropylcellulose L (low viscosity) are suspended therein and this mixture is cooled and stirred until completely dissolved. 720 g of microfinely ground nimodipine of modification II are suspended therein. The suspension (2,400 g) is ground by means of a bead mill with cooling to give an average particle size of about 0.85 μm. In a separate vessel, 8 g of Solbrol M, 10 g of citric acid, 20 g of sodium citrate and 122 g are dissolved in 8012 g of demineralised water. 2000 g of the ground suspension are added to this solution at room temperature and it is stirred. Drops are formed which, after storage for over 1 year, show no change in the physical characteristics or particle size.

Example 4: (Solid pharmaceutical form)

4 g of hydroxypropylcellulose L and 18 g of Texapon K 12 are dissolved in 1040 g of water. 600 g of micronised nimodipine modification II are suspended therein and ground by means of a bead mill to an average particle size of about 0,3 μm. 135 g of hydroxypropylcellulose L are dissolved in 1500 g. 1260 g of the bead-ground nimodipine suspension are added to this solution. 450 g of Avicel, 561 g of lactose and 300 g of AC-Di-Sol are initially introduced into a fluidised bed granulator, the abovementioned suspension is sprayed, and the granules obtained are sieved and mixed with 465 g of Avicel, 300 g of Plasdone XL and 9 g of magnesium stearate. The mixture is compressed to give tablets having a total weight of 270 mg and contain 45 mg of nimodipine modification II per tablet. The tablets are coated.

We claim:

1. A stable pharmaceutical preparation comprising a suspension of a pharmaceutically acceptable suspending liquid and a conglomeritic mixture of crystals of isopropyl-(2-methoxyethyl) 1,4-dihydro-2,6-dimethyl-4-(3-nitrophenyl)-3,5-pyridinedicarboxylate, said crystals having the crystalline structure of modification II, having a melting point of 116° C. and an average particle size of at most 5 μm.

2. In the method of treating a patient suffering from a cerebral disorder by administering to said patient an effective amount therefor of a pharmaceutical preparation containing nimodipine, wherein the improvement comprises administering as the pharmaceutical preparation the stable pharmaceutical preparation according to claim 1.

* * * * *